(12) United States Patent
Offenbacher

(10) Patent No.: US 6,808,619 B2
(45) Date of Patent: Oct. 26, 2004

(54) ELECTRODE SYSTEM

(75) Inventor: Helmut Offenbacher, Graz (AT)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 09/860,073

(22) Filed: May 17, 2001

(65) Prior Publication Data

US 2002/0005352 A1 Jan. 17, 2002

Related U.S. Application Data

(63) Continuation of application No. PCT/AT99/00279, filed on Nov. 18, 1999.

(30) Foreign Application Priority Data

Nov. 19, 1998 (AT) .............................. 1930/98

(51) Int. Cl.$^7$ ..................... G01N 27/30; G01N 27/49
(52) U.S. Cl. .................. 205/783; 205/794.5; 204/415; 204/431; 204/403.01; 204/403.15
(58) Field of Search ................ 204/403, 415, 204/418, 431, 432, 403.01, 403.15; 205/794.5, 783

(56) References Cited

U.S. PATENT DOCUMENTS

| | | | | |
|---|---|---|---|---|
| 4,072,594 A | * | 2/1978 | Outsuka et al. ............. 204/406 |
| 5,231,028 A | * | 7/1993 | Mullen ........................ 205/188 |
| 5,582,697 A | * | 12/1996 | Ikeda et al. ............... 205/777.5 |
| 5,804,047 A | * | 9/1998 | Karube et al. ......... 204/403.04 |
| 6,040,077 A | * | 3/2000 | Debe et al. .................... 429/40 |
| 6,183,907 B1 | * | 2/2001 | Barusseau et al. .......... 429/217 |
| 6,214,185 B1 | * | 4/2001 | Offenbacher et al. .......... 435/4 |
| 6,225,078 B1 | * | 5/2001 | Ikeda et al. ................. 204/403 |
| 6,248,224 B1 | * | 6/2001 | Kitzelmann ................. 204/414 |
| 6,326,160 B1 | * | 12/2001 | Dunn et al. ................. 204/400 |
| 6,340,597 B1 | * | 1/2002 | Svorc et al. ............. 204/403.1 |

FOREIGN PATENT DOCUMENTS

| | | |
|---|---|---|
| EP | 0078636 | 5/1983 |
| EP | 0528557 | 2/1993 |
| EP | 0593990 | 4/1994 |
| EP | 0603154 | 6/1994 |
| WO | 0031524 | 6/2000 |

OTHER PUBLICATIONS

English–language Abstract for JP 02 090 052. Mar. 1990.
English–language Abstract for JP 59 026 052. Feb. 1984.

* cited by examiner

Primary Examiner—Kaj K. Olsen
(74) Attorney, Agent, or Firm—Roche Diagnostics Operations, Inc.

(57) ABSTRACT

In an electrode system, particularly for electrochemical sensors, which comprises a working electrode, a counter-electrode and an electrolyte, the counterelectrode is constituted by a material containing an elementary carbon, whereby the long-term stability of the electrode system is considerably increased (FIG. 2).

20 Claims, 4 Drawing Sheets

ELECTRODE SYSTEM

This is a continuation of copending application Ser. No. PCT/AT99/00279 filed Nov. 18, 1999, which is incorporated by reference herein. PCT/AT99/00279 was not published in English.

INTRODUCTION

The invention relates to an electrode system, particularly for electrochemical sensors, which comprises a working electrode, a counterelectrode and an electrolyte.

Such an electrode system is used for example in the oxygen electrode of Clark.

BACKGROUND OF THE INVENTION

The oxygen electrode of Clark is used for measuring the partial pressure of oxygen in the blood, among other uses. The blood gas analysis is an important branch of medical diagnostics and is able to give evidence of the state of the cardiovascular system as well as of metabolic processes in the organism.

For determining the partial pressure of oxygen in the blood and other biological media there are used sensor systems based either on the principle of electrochemical sensor technology, such as amperometry, or on the principle of dynamic fluorescence quenching. The oxygen electrode of Clark is a representative of the first-named group.

The principle of the oxygen electrode of Clark is based on the reaction (reduction) of $O_2$ to $OH^-$ on a platinum electrode in the presence of $H_2O$. As anodic counterreaction, the release of silver ions on a silver anode is usually, but not exclusively, utilized.

The service life of such a sensor system depends on a series of factors. However, a limitation that is essential in practice arises due to the deposition at the cathode of the silver released at the anode. Thereby, the polarizability of the cathode is suppressed, which leads to unwanted side-reactions and an increasing inactivation of the electrode. As a rule, an electrode thus inactivated can only be regenerated by mechanical measures. However, while miniaturizing an oxygen electrode of Clark and making it maintenance-free as desired, a mechanical regeneration becomes nearly impossible.

A number of possibilities are known to extend the service life of a sensor system of the kind of the oxygen electrode of Clark. On the one hand, it is tried to keep the silver concentration as low as possible by means of appropriate salt solutions. On the other hand, the diffusion of the silver to the cathode is inhibited as well as possible by mechanical and chemical measures. These, however, are only dilatory measures.

Another possibility of extending the service life consists in the use of gold or platinum as anode material. However, such anodes are polarizable and, as a consequence, do not give stable potentials in the long run. The service life of such electrode systems is several weeks. If, on the contrary, non-polarizable metals are used, there again occur corresponding depositions at the cathode and/or surface changes at the anode.

The silver deposition problem is particularly serious in miniaturized oxygen electrodes that are manufactured according to the principle of the planar technique, where the immediate vicinity of the silver anode to the platinum cathode as well as the small amount of electrolyte that is available result within a very short time in the inactivation of the cathode, due to silver deposition.

In EP-A-0 603 154 for example there is described an amperometric enzyme electrode for measuring the concentration of an enzyme substrate, wherein the decomposition of $H_2O_2$ to $H^+$ and oxygen is measured amperometrically in a known manner. The electrode material of the working electrode consists in a redox-inactive conductor with a conductive pigment, a binding agent that is not conducting itself and a catalytically active substance finely distributed therein. As catalytically active substance, manganese dioxide deposited on graphite or activated charcoal may be contemplated, for example. The catalytically active substance suppresses interferences when the enzyme substrate is measured. As counterelectrode, a conventional silver/silver chloride electrode with the known disadvantages is used in this known system.

SUMMARY OF THE INVENTION

The invention has as its object to avoid the problems of the known electrode systems and to provide an electrode system which has an improved long-term stability. In particular, it should be possible to use the electrode system for a miniaturized oxygen electrode.

According to the invention, in an electrode system, particularly for electrochemical sensors, which comprises a working electrode, a counterelectrode and an electrolyte, this object is achieved in that the counterelectrode is constituted by a material containing an elementary carbon.

In the electrode system according to the invention, the service life has shown itself as being considerably increased, which is due to the fact that at the working electrode there do not occur depositions, which diminish the polarizability of the working electrode and lead to unwanted side-reactions at the working electrode. At the same time, however, the potential of the counterelectrode remains stable over a long time period thanks to the inventive measure.

Although an electrode constituted by a material containing a carbon exhibits, in principle, the phenomenon of polarizability like an electrode with gold or platinum as electrode material, it has surprisingly been found that the long-term stability of the electrode system according to the invention is clearly higher than that of a conventional electrode system.

According to a preferred embodiment of the invention, the counterelectrode is connected as anode.

DETAILED DESCRIPTION OF THE INVENTION

Figure 1:
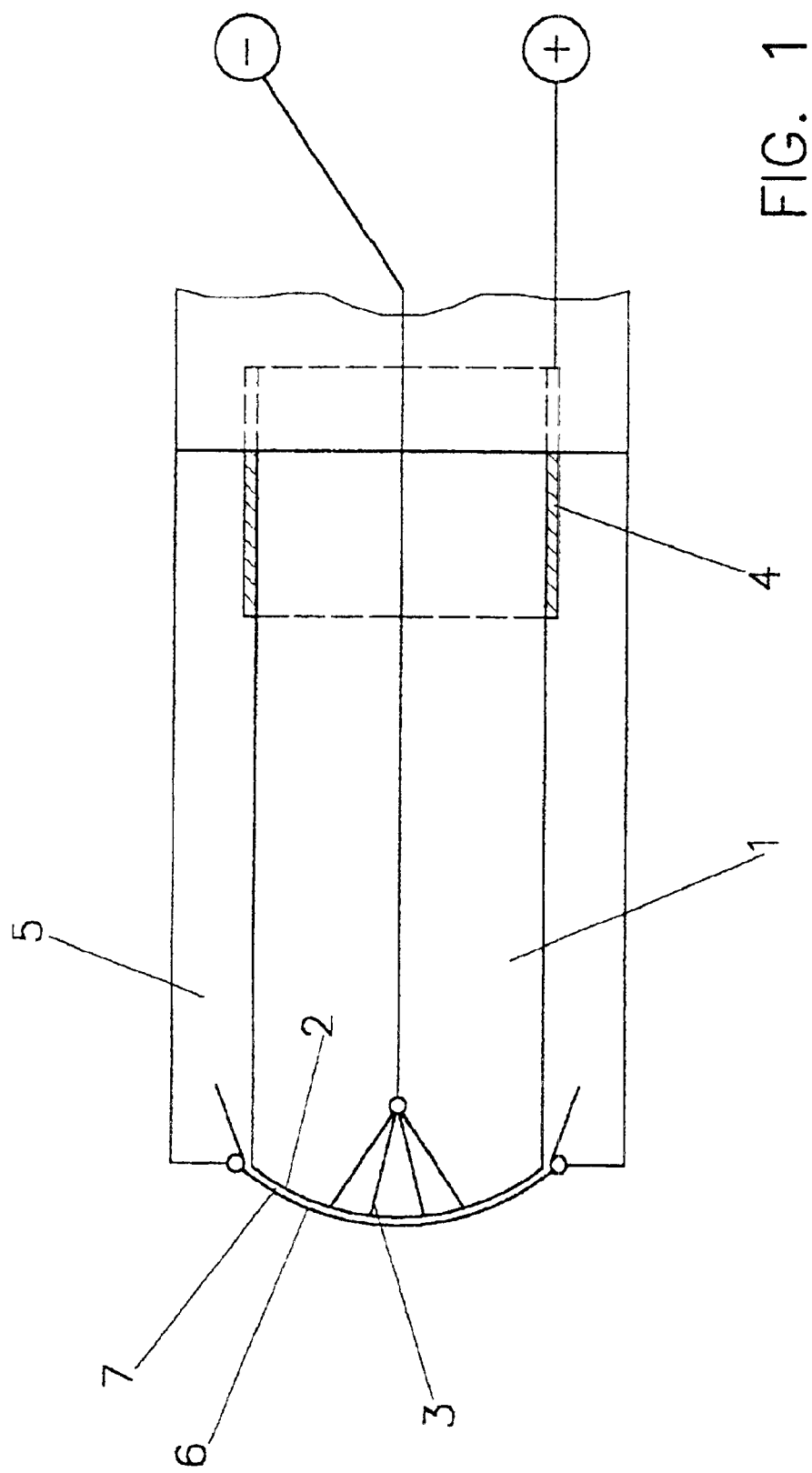
FIG. 1 depicts the construction principle of an oxygen electrode of Clark.

The electrode system according to the invention is preferably used for an amperometric oxygen sensor, in particular for a miniaturized amperometric oxygen sensor. The problem of the rapid inactivation, which is particularly serious in a miniaturized amperometric oxygen sensor, can be effectively avoided by using the electrode system according to the invention.

Whereas for example noble-metal anodes in a known oxygen electrode of Clark involve a division in half of the current flow within 3 to 4 months at the latest when the operating voltage is applied and the oxygen concentration ($pO_2$) is constant, e.g. air level, the elementary-carbon-based electrodes according to the invention exhibit a constant flow of current up to about 6 months. Only after 7 to 9 months, the current flow drops below a value which is necessary for a sufficiently exact oxygen measurement.

In an amperometric oxygen sensor, the electrode reaction taking place at the anode while the electrode system according to the invention is being used substantially is a reversion of the cathode reaction, as has been shown by polarographic studies on electrode systems with separated electrolyte spaces at varied pH and $pO_2$ values. The inventive electrode material, which contains elementary carbon, has good adsorber properties for oxygen, which has advantageous effects on the long-term stability of the electrode system.

In the inventive electrode system, the electrode material of the counterelectrode preferably comprises a mixture of elementary carbon and at least one polymer. Here, the elementary carbon is preferably graphite and/or soot and/or graphite fiber and/or glassy carbon.

It turned out that for example an addition of soot enlarges the active electrode surface and extends the service life of the electrode system. Particularly electrodes with a graphite-fiber electrode material exhibit very good long-term-stability properties. They stand out by a current constancy over a time period of more than 18 months. However, with these electrode materials, sealing is difficult.

The polymer is preferably selected from a group comprising vinyl resins, polyolefins, silicones, elastomers on the basis of polyurethanes, polybutadiene or butadiene copolymers, in particular nitrilobutyl rubber. With a view to the long-term stability of the electrode systems, vinyl resins and nitrilobutyl rubber are particularly preferred.

Suitably, the polymer contains additives, in particular softeners, extrusion auxiliaries and stabilizers.

Preferably, the electrode material of the counterelectrode is a paste which optionally is suitable for screen printing. This allows preparing the counterelectrode in a simple manner. By immersing, stencilling or screen-printing, the electrode material can be applied in the form of a solvent-containing screen-printing paste onto a support.

According to another preferred embodiment, the electrode material of the counterelectrode is a mixture suitable for injection molding, comprising carbon and a polymer that is thermoplastic or a polymer that cross-links into a duroplast. Hereby, simple electrode manufacturing is likewise made possible.

The electrode material of the counterelectrode and/or the electrolyte preferably comprise(s) at least one mediator. Addition of a mediator drastically reduces the so-called aging of the electrode surface, so that for example in an oxygen sensor system the duration of the current constancy could be extended to 12 to 18 months when the operating voltage was permanently applied. Such a mediator effect could not-or not to a significant extent-be observed with an oxygen electrode with a gold anode.

The mediator preferably can be a transition metal complex, the metal being selected from a group comprising manganese, iron, cobalt and vanadium. Further, the mediator preferably can be a transition metal complex of the cyclopentadienide anion, in particular ferrocene or a derivative thereof. According to another preferred embodiment, the mediator is dimethyl ferrocene dicarboxylate, the hydrolysis product thereof or a salt of ferrocene dicarboxylic acid. According to a further preferred embodiment, the mediator is a manganese(II), cobalt(II) or vanadium(IV) complex of phthalocyanine or a Mn(III) or cobalt(II) complex of 2,3,7,8,12,13,17,18-octaethyl-21H,23H-porphine or iron hexacyanoferrate. The mediator can also be a transition metal oxide, preferably of medium valence, in particular manganese dioxide. Furthermore, the mediator can preferably be tetrathiafulvalene, 7,7,8,8-tetracyanoquinodimethane, or a derivative or complex thereof, in particular a 1:1 complex of tetrathiafulvalene and 7,7,8,8-tetracyanoquinodimethane. With a view to the long-term stability of the electrode systems, ferrocene, dimethyl ferrocene dicarboxylate and manganese dioxide are particularly preferred among these mediators.

Preferably, the mediator is present in the electrode material of the counterelectrode in a concentration ranging from about 1% to about 30% and/or is present in the electrolyte in a concentration of 3 mol/l at the most. Suitably, the mediator is introduced into the electrode material prior to electrode preparation.

In particular, the electrode material of the counterelectrode preferably comprises a mixture of carbon and nitrilobutyl rubber and the electrolyte, dimethyl ferrocene dicarboxylate as mediator. According to another particularly preferred embodiment, the electrode material of the counterelectrode comprises a mixture of graphite and vinyl resin and the electrolyte, dimethyl ferrocene dicarboxylate as mediator. According to a further particularly preferred embodiment, the electrode material of the counterelectrode comprises a mixture of graphite and vinyl resin as well as manganese dioxide as mediator. An electrode system with graphite-fiber electrode material is also particularly preferred. With the above-named electrode systems, a current constancy over a particularly long period of time is ensured.

In the electrode system according to the invention, the electrolyte preferably contains ethylene glycol and/or water as solvent as well as sodium chloride as conducting salt and/or a phosphate buffer.

In the following, the invention will be explained in more detail by way of the drawings (FIGS. 1 to 5) and by way of exemplary embodiments.

In FIG. 1, the construction principle of an oxygen electrode of Clark is represented diagrammatically. The oxygen electrode consists of a cylindrical glass body 1, whose front surface 2 has a spherical-cap form. At this front surface, 2, one or several noble-metal wires 3, preferably platinum wires, which are connected as cathode, emerge to the surface of glass body 1. At the shank portion of glass body 1, an anode 4 of sheet silver is arranged cylindrically. Glass body 1 is surrounded by an electrolyte, formed of a conducting salt and a buffer salt system, in electrolyte space 5.

In front-surface area 2 a gas-permeable (Teflon) membrane 6 lies close to glass body 1 so as to ensure a thin electrolyte gap 7 between glass body 1 and membrane 6. In this electrolyte gap, 7, the gas components penetrating through membrane 6 dissolve. The oxygen itself diffuses according to the $O_2$ concentration gradient to the cathode and is reacted there to become OH. The buffer capacity of the electrolyte makes that the pH value in the cathode region does not rise too much during oxygen reaction. The diffusion of the electrolyte ions provides for a regeneration of the buffer system in situ and thus inhibits the collapse of the buffer system in electrolyte gap 7 when the buffer capacity is spent. In this electrolyte gap, 7, there flows of course also an ion stream, which is equivalent to the electron stream required for the $O_2$ reduction.

In accordance with the invention, an oxygen electrode of Clark has been modified in that the silver anode has been replaced by a material containing an elementary carbon.

The following electrode materials have been tested:

A. Mediator-free Graphite Pastes
  1. Graphite 50–70% in a screen-printing paste whose polymer binding agent is a vinyl resin (=graphite paste)
  2. Graphite paste+5–10% flame soot, based on the paste solid (=graphite and polymer component)

By graphite paste (carbon paste), a material with 50±10% carbon polymer and 50±10% solvent is understood here.

B. Mediator-containing Graphite Pastes
  1. Graphite paste+1% ferrocene, based on the paste solid
  2. Graphite paste+1% TTF-TCNQ complex (=tetrathiafulvalene-7,7,8,8-tetracyanoquinodimethane complex), based on the paste solid
  3. Graphite paste+1% Prussian blue (iron hexacyanoferrate), based on the paste solid
  4. Graphite paste+10–30% manganese dioxide, based on the paste solid C. Conductive Thermo- and/or Duroplastic Carbon-polymer Systems Suitable for Injection Molding,
  1. Polyolefins
  2. Nitrilobutyl rubber (NBR=nitrilobutyl rubber)
  3. a hot-cross-linking silicone 2-component system being used as polymers.

As electrolyte there has been chosen a system whose solvent consisted of 90% by weight ethylene glycol and 10% by weight water, which had a conducting-salt (NaCl) concentration of 80 mmol/l and a phosphate-buffer concentration of 16 mmol/l. The ratio of primary to secondary phosphate was varied in such a way that electrolytes having pH values of between 6.3 and 7.8 resulted.

The mediator-containing electrode materials of group B were tested with mediator-free electrolytes and the mediator-free electrode materials of groups A and C were tested with electrolytes doped with the mediators indicated below. The concentration of the mediators corresponded to the saturation concentration in the electrolyte but its upper limit was set at 3 mmol/l.

The following mediators in the electrolyte have been tested: ferrocene, 1,1-dimethyl ferrocene dicarboxylate, TTF (tetrathiafulvalene), TCNQ (7,7,8,8-tetracyanoquinodimethane), TTF-TCNQ complexes, Prussian blue (iron hexacyanoferrate), phthalocyanine complexes of Mn(II), cobalt(II) and vanadium(IV) as well as Mn(III) and cobalt(II) complexes of 2,3,7,8,12,13,17,18-octaethyl-21H,23H-porphine.

When using graphite-vinyl resin pastes as electrode material, these were applied onto a support. Electrode materials suitable for injection molding by injection-molding processes were processed into cylindrical or horseshoe-shaped electrode bodies, which were contacted outside the electrolyte space.

The oxygen electrodes of Clark modified with the electrode materials according to the invention in long-term tests were tested at a voltage applied of 700 mV at room temperature, the electrodes being exposed to a water-saturated air atmosphere.

Testing of the electrodes was done by way of long-term observation of the current course, by recording a polarogram one time a month and observing its change as well as by registration of the dependence of the current flow on the $O_2$ partial pressure. For the latter test the following measuring media were used:

for $pO_2$=0 mm Hg, a bisulfite solution;

for $pO_2$=158 torr, air-saturated water;

for $pO_2$=760 torr, a water tonometrized with $O_2$.

By tonometrized water, water equilibrated with a calibrating or measuring gas is understood here.

Optimized systems have been tested under instrument conditions for their suitability in the form of a miniaturized oxygen electrode of Clark.

The following results have been achieved:

As compared with conventional oxygen electrodes of Clark, all of the oxygen electrodes with anode material on a carbon-polymer basis showed a mostly identical polarogram and approximately the same current intensities at identical $pO_2$ values.

Both mediators and the enlargement of the active surface by addition of soot substantially exercised a positive influence on the aging of the electrodes.

Figure 2:
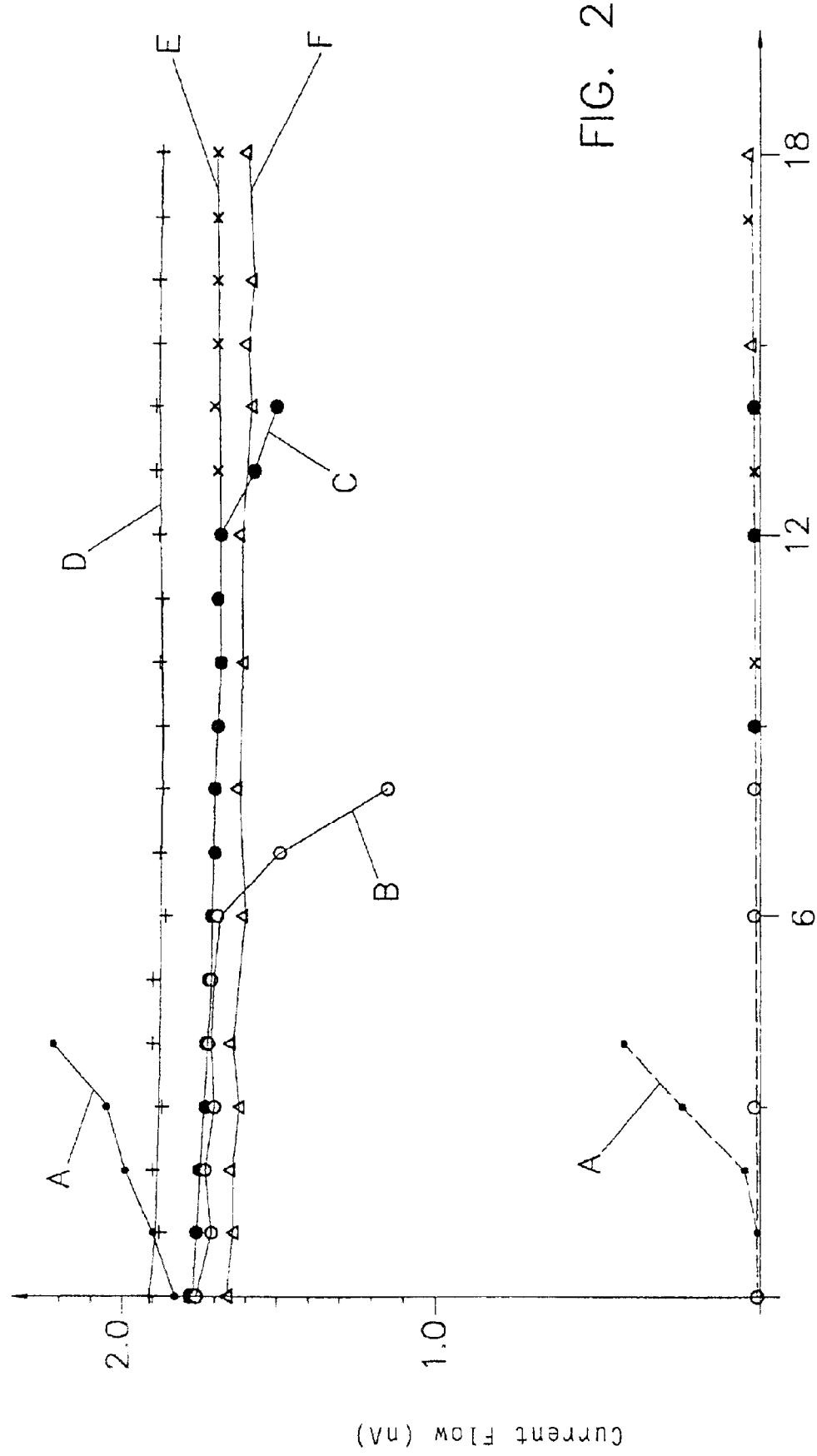
FIG. 2 depcits the chronological development of the current intensity of oxygen electrodes when different anode materials are used.

In FIG. 2 there is represented the chronological development of the current intensity of oxygen electrodes at $pO_2$=158 mm Hg (–) or $pO_2$=0 mm Hg ( . . . ) when different anode materials are used:

(A) Silver anode and mediator-free internal electrolyte (B) Graphite-vinyl resin as anode material and mediator-free internal electrolyte (C) Graphite-vinyl resin as anode material and ferrocene in the electrolyte (D) Carbon-NBR as anode material and dimethyl ferrocene dicarboxylate in the electrolyte (E) Graphite-vinyl resin-$MnO_2$ as anode material and mediator-free electrolyte (F) Carbon fiber as anode material and mediator-free electrolyte For long-term tests at room temperature and at a permanently applied operating voltage of 700 mV, the electrodes were exposed to an oxygen level of 158 mm Hg (air).

As can been seen in FIG. 2, electrode systems having ferrocene or dimethyl ferrocene dicarboxylate added in the electrolyte (C or D in FIG. 2) as well as electrode systems having manganese dioxide ($MnO_2$) added in the anode material (E) or graphite fiber anode (0.2 g/anode; F in FIG. 2) gave particularly good results. When using graphite fiber, the service life for example was more than 18 months thanks to the large active surface of the anode.

Figure 3:
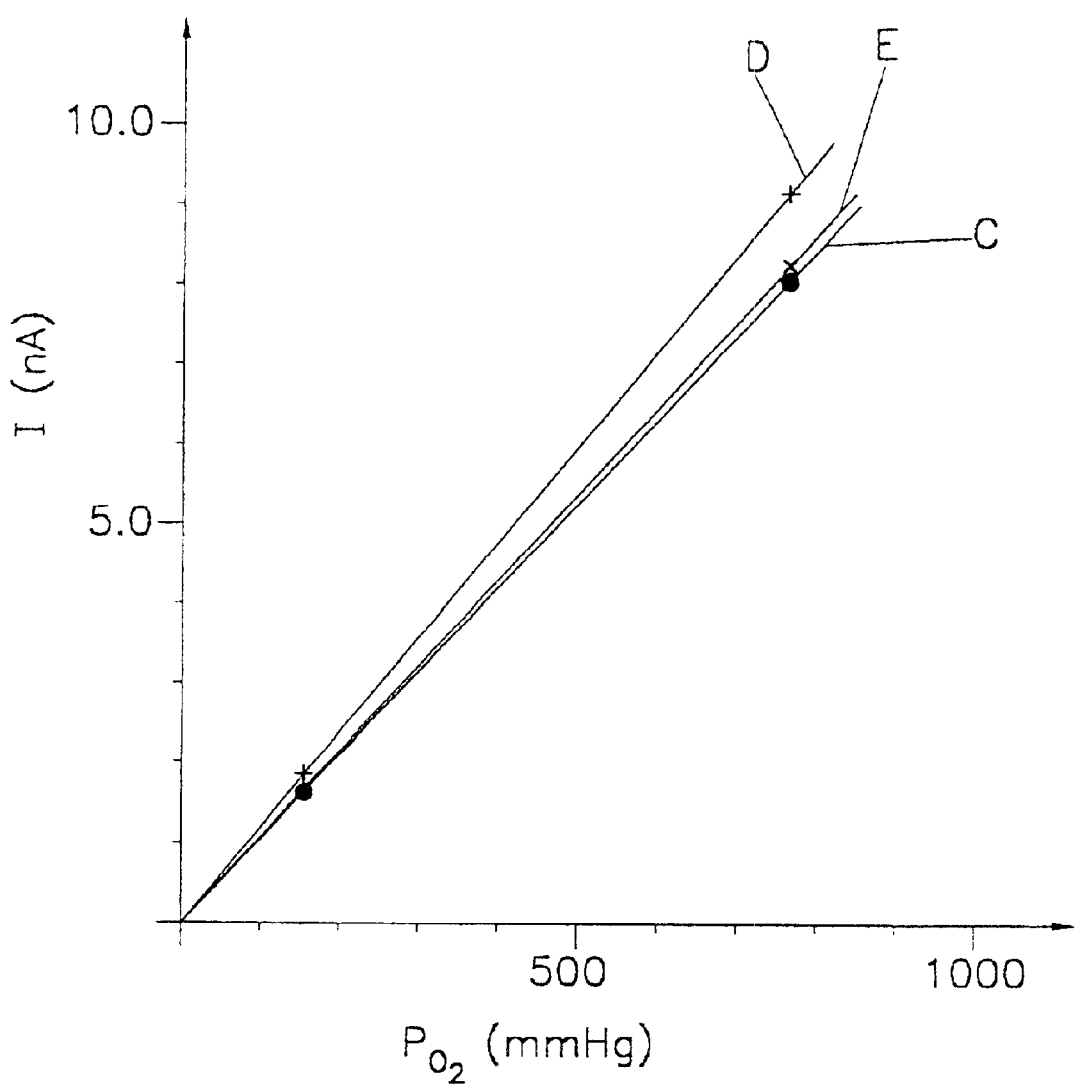
FIG. 3 depicts the relationship between current flow and oxygen partial pressure for various electrode systems.
Figure 4:
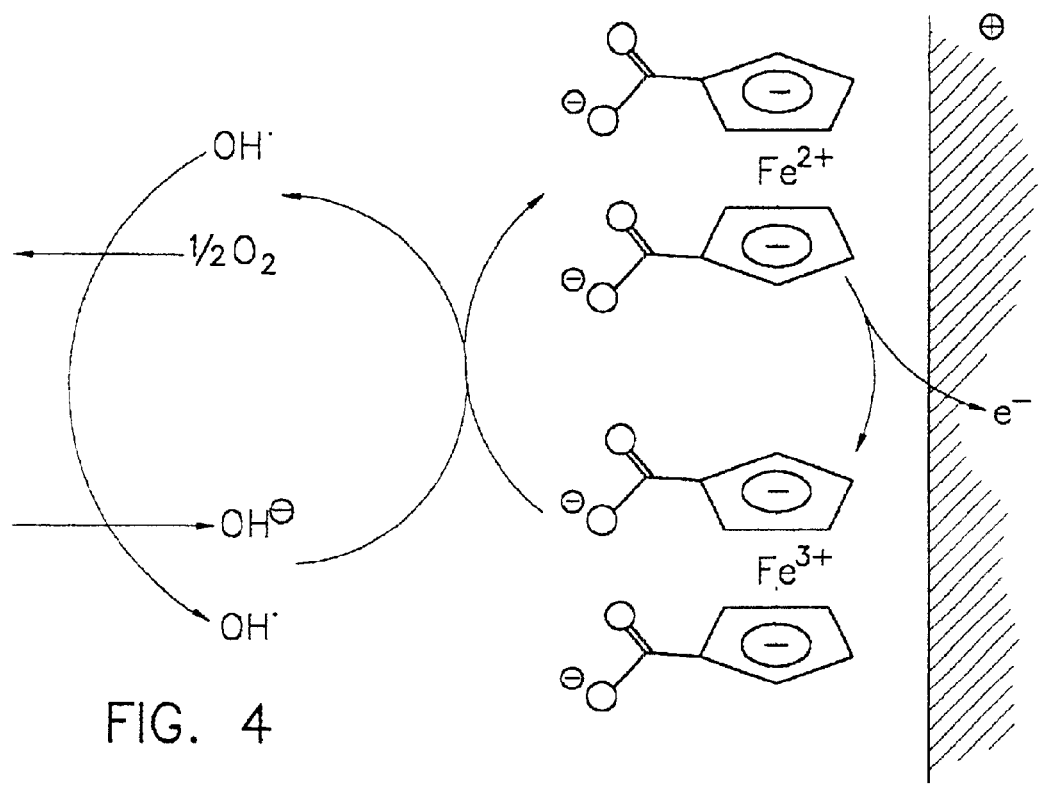
FIG. 4 depicts a schematic diagram of the reaction at the anode.

The dependence of the current flow on the oxygen partial pressure was strictly linear and did not change during the observation period. In FIG. 3, the strictly linear dependence of the current flow on the oxygen partial pressure is represented for the electrode systems (C), (D) and (E) after 12 months of operation. Obviously, the mediators did not have an influence on the cathode reaction.

Whereas electrodes with the Mn(III) complex of the 2,3,7,8,12,13,17,18-octaethyl-21H,23H-porphine in the electrolyte showed the maximum current flow to be expected only after a month, the other tested electrode systems were fully operative after a short period of polarization.

As compared with the systems whose anode was prepared from pure graphite pastes and whose electrolyte was mediator-free (B in FIG. 2), all of the indicated mediator-containing electrode systems showed a clear extension in time of the current constancy. It turned out that soot additions likewise involved an extension of the service life by almost two months, due to the enlargement of the active anode surface.

From FIG. 2 it is apparent that graphite (soot) vinyl resin anodes as well as the carbon-nitrilobutyl rubber (NBR) anodes in combination with ferrocene, dimethyl ferrocene dicarboxylate or manganese dioxide as mediators are very suitable for the use in oxygen electrodes that are stable in the long run. Dimethyl ferrocene dicarboxylate was particularly suitable as mediator as this compound had, as compared to other mediators, such as ferrocene, a relatively good solubility in the electrolyte and exhibited a significantly lower inclination towards deactivation, caused by side-reactions.

It is to be supposed that the dimethyl ester of the ferrocene dicarboxylic acid hydrolyses particularly quickly to the ferrocene dicarboxylate in the cathode region and, in a longer period of time and to a large extent, in the electrolyte as well. This ion in the oxidized form has a simple negative charge and therefore is ineffective at the cathode, due to electrostatic repulsion. At the anode, the reaction scheme represented in FIG. 4 may be postulated.

When using ferrocene in the electrolyte and/or in the anode material, the service life of an electrode system was 12 months at the most. It could be observed that the drop of the current flow was accompanied by a decoloration of the electrolyte, colored yellow by the mediator. A substitution of the electrolyte reestablished the operability of the electrode system. Hence, the function of the mediator was decisive for the service life.

Electrodes with carbon-NBR anodes, combined with dimethyl ferrocene dicarboxylate in the electrolyte, and $MnO_2$-containing graphite-vinyl resin anodes, combined with mediator-free electrolytes, showed a service life of 15 to 18 months at optimum current intensities (90–100% of the current intensity measured in a geometrically analogous conventional oxygen electrode of Clark with a silver anode).

An essential advantage of the use of the inventive electrode materials for the counterelectrode, or in the specific case of the oxygen electrode for the anode, and of the electrode or anode mediator systems is to avoid the silver deposition, often problematic with the oxygen electrode of Clark, as initially mentioned. The application of the electrode systems according to the invention (with or without mediator) involves numerous advantages, particularly in the development of so-called planar thick-layer oxygen sensors, in which the distance between anode and cathode is short and the electrolyte gap is large as compared to the classic electrode type.

The graphite-polymer-$MnO_2$ electrode system has turned out to be particularly favorable for this application.

Figure 5:
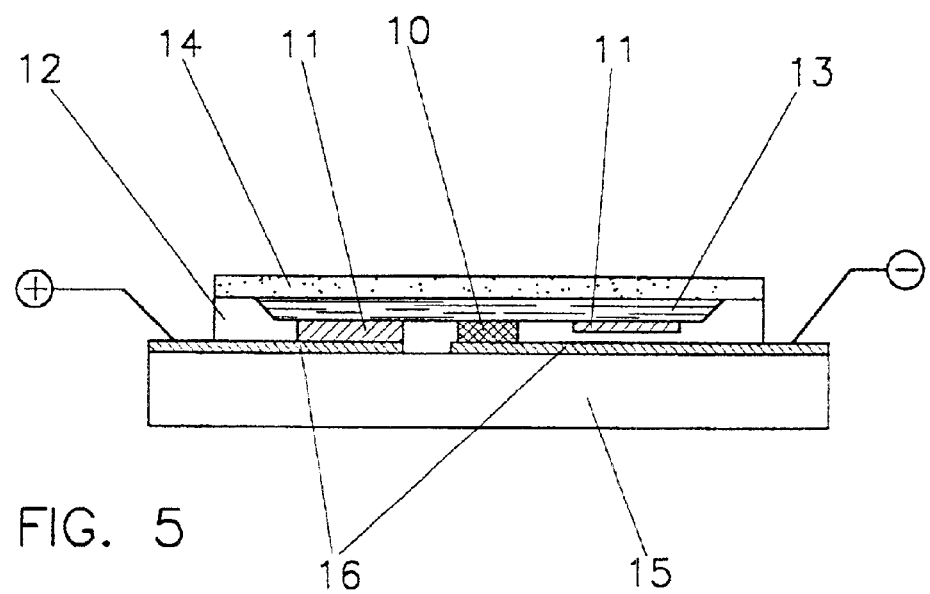
FIG. 5 depicts a diagrammatic view of a thick-layer oxygen sensor.

As an example, FIG. 5 shows a diagrammatic view of such a thick-layer oxygen sensor. In FIG. 5 there are represented a cathode spot 10, symmetrically arranged areal anodes 11, an insulation layer 12, an electrolyte layer 13, a gas-permeable membrane 14, a support 15 and conducting sheets 16. Thick-layer oxygen sensors of this type were tested under instrument conditions for their suitability regarding long-term stability while using the electrode materials according to the invention and/or the mediators in the electrolyte; as stated above, very good results were achieved.

The present invention is not limited to the represented exemplary embodiments but also comprises all variations coming within the scope of the annexed claims.

What is claimed is:

1. An electrode system comprising
a working electrode which functions as a cathode,
a counterelectrode which functions as an anode, and
an electrolyte, wherein
the counterelectrode comprises an electrode material comprising a mixture of elemental carbon, a mediator and at least one polymer and
the electrolyte comprises at least one mediator.

2. An electrode system according to claim 1, wherein the elemental carbon is selected from the group consisting of graphite, soot, graphite fibre, glassy carbon and combinations thereof.

3. An electrode system according to claim 1, wherein the polymer is selected from a group consisting of vinyl resins, polyolefins, silicones, elastomers on the basis of polyurethanes, polybutadiene, butadiene copolymers and nitrilobutyl rubber.

4. An electrode system according to claim 1, wherein the polymer contains additives selected from the group consisting of softeners, extrusion auxiliaries and stabilizers.

5. An electrode system according to claim 1, wherein the counterelectrode is a paste comprising the mixture of elemental carbon and the at least one polymer applied to a support, optionally by screen printing.

6. An electrode system according to claim 1, wherein the electrode material of the counterelectrode obtained by injection molding a mixture comprising carbon and a polymer selected from the group consisting of a polymer that is thermoplastic and a polymer that cross-links into a duroplast.

7. An electrode system according to claim 1, wherein the mediator of the electrolyte is a transition metal complex, the metal being selected from a group consisting of manganese, iron, cobalt and vanadium.

8. An electrode system according to claim 7, wherein the mediator of the electrolyte is selected from the group consisting of a manganese (II) complex of phthalocyanine, a cobalt (II) complex of phthalocyanine, a vanadium (IV) complex of phthalocyanine, a manganese (Ill) complex of 2,3,7,12,13,17,18-octaethyl-21H,23-H-porphine, a cobalt (II) complex of 2,3,7,8,12,13,17,18-octaethyl-21H,23-H porphine, and hexacyanoferrate.

9. An electrode system according to claim 1, wherein the mediator of the electrolyte is a transition metal complex of the cyclopentadienide anion.

10. An electrode system according to claim 1, wherein the mediator of the electrolyte is selected from the group consisting of dimethyl ferrocene dicarboxylate, the hydrolysis product of dimethyl ferrocene dicarboxylate and a salt of ferrocene dicarboxylic acid.

11. An electrode system according to claim 1, wherein the mediator of the electrolyte is a transition metal oxide.

12. An electrode system according to claim 1, wherein the mediator of the electrolyte is selected from the group consisting of tetrahiafulvalene, 7,7,8,8-tetracyanoquinodimethane, derivatives thereof and complexes thereof.

13. An electrode system according to claim 1, wherein the mediator is present in the electrode material of the counterelectrode in a concentration ranging from about 1% to about 30% by weight of the electrode material.

14. An electrode system according to claim 1, wherein the mediator is present in the electrolyte in a concentration of less than or equal to 3 mmol/l.

15. An electrode system according to claim 1, wherein the at least one polymer comprises nitrilobutyl rubber and the at least one mediator of the electrolyte comprises dimethyl ferrocene dicarboxylate.

16. An electrode system according to claim 1, wherein the electrode material of the counterelectrode comprises a mixture of graphite and vinyl resin and the mediator of the electrolyte comprises dimethyl ferrocene dicarboxylate.

17. An electrode system according to claim 1, wherein the electrode material of the counterelectrode comprises a mixture of graphite and vinyl resin, and the mediator of the electrode material comprises manganese dioxide.

18. An electrode system according to claim 1, wherein the electrolyte contains a solvent selected from the group consisting of ethylene glycol, water and combinations thereof.

19. An electrode system according to claim 1, whrein the electrolyte contains a substance selected from the group consisting of sodium chloride as conducting salt and a phosphate buffer.

20. A method of measuring the partial pressure of oxygen in a solution comprising contacting the solution with an electrode system and then measuring the current flow in the electrode system and determining the partial pressure of oxygen from the measured current flow, wherein the electrode system comprises a working electrode which functions as a cathode, a counterelectrode which functions as an anode and an electrolyte, wherein (i) the counterelectrode comprises an electrode material comprising a mixture of elemental carbon and at least one polymer and (ii) the electrolyte comprises at least one mediator.

* * * * *